(12) United States Patent
Saint-Martin

(10) Patent No.: US 8,845,695 B2
(45) Date of Patent: *Sep. 30, 2014

(54) ANCHORING MEMBER WITH SAFETY RING

(75) Inventor: Pierre Henri Saint-Martin, Merignac (FR)

(73) Assignee: Stryker Spine (FR)

( * ) Notice: Subject to any disclaimer, the term of this patent is extended or adjusted under 35 U.S.C. 154(b) by 234 days.

This patent is subject to a terminal disclaimer.

(21) Appl. No.: 13/429,916

(22) Filed: Mar. 26, 2012

(65) Prior Publication Data

US 2012/0179206 A1 Jul. 12, 2012

Related U.S. Application Data

(63) Continuation of application No. 12/658,838, filed on Feb. 16, 2010, now Pat. No. 8,167,916, which is a continuation of application No. 10/096,991, filed on Mar. 13, 2002, now Pat. No. 7,686,834.

(30) Foreign Application Priority Data

Mar. 15, 2001 (FR) ..................................... 01 03515

(51) Int. Cl.
*A61B 17/88* (2006.01)
*A61B 17/70* (2006.01)

(52) U.S. Cl.
CPC ......... *A61B 17/7037* (2013.01); *A61B 17/7032* (2013.01)
USPC ....................................................... 606/279

(58) Field of Classification Search
CPC ........... A61B 17/7037; A61B 17/7032; A61B 17/7035; A61B 17/8605; A61B 17/7049; A61B 17/683; A61B 17/7002; A61B 17/7088; A61B 17/7043; A61B 17/1744
USPC ......... 606/279, 278, 267, 266, 269, 270, 246, 606/264, 265, 268, 271, 272, 273, 274, 275, 606/301, 305, 307, 308

See application file for complete search history.

(56) References Cited

U.S. PATENT DOCUMENTS

| 4,413,512 A | 11/1983 | Zemanek, Jr. |
| 4,719,423 A | 1/1988 | Vinegar et al. |

(Continued)

FOREIGN PATENT DOCUMENTS

| DE | 197 20 782 A1 | 11/1998 |
| DE | 299 03 342 U1 | 6/1999 |

(Continued)

OTHER PUBLICATIONS

French Preliminary Search Report dated Nov. 27, 2001.

*Primary Examiner* — Pedro Philogene
(74) *Attorney, Agent, or Firm* — Lerner, David, Littenberg, Krumholz & Mentlik, LLP

(57) ABSTRACT

A method for osteosynthesis of a spinal column using an assembly including a bone anchor, a connector and a ring, the method comprising: inserting an anchoring part of the bone anchor into bone, the bone anchor including the anchoring part and a head, the head positioned to be in contact with the connector and ring; inserting a connecting member into the connector; and applying a force to the connecting member such that the connecting member applies the force against the ring and the bone anchor, wherein the head of the bone anchor contacts the connector, ring and connecting member during the application of the force.

20 Claims, 4 Drawing Sheets

(56) References Cited

U.S. PATENT DOCUMENTS

| | | | |
|---|---|---|---|
| 5,212,447 A | 5/1993 | Paltiel | |
| 5,466,237 A * | 11/1995 | Byrd et al. | 606/272 |
| 5,690,630 A | 11/1997 | Errico et al. | |
| 5,879,350 A | 3/1999 | Sherman et al. | |
| 5,885,286 A | 3/1999 | Sherman et al. | |
| 5,891,145 A * | 4/1999 | Morrison et al. | 606/266 |
| 6,010,503 A | 1/2000 | Richelsoph et al. | |
| 6,053,917 A | 4/2000 | Sherman et al. | |
| 6,074,391 A | 6/2000 | Metz-Stavenhagen et al. | |
| 6,090,111 A | 7/2000 | Nichols | |
| 6,280,442 B1 | 8/2001 | Barker et al. | |
| 6,331,179 B1 | 12/2001 | Freid et al. | |
| 6,402,752 B2 * | 6/2002 | Schaffler-Wachter et al. | 606/266 |
| 6,471,705 B1 | 10/2002 | Biedermann et al. | |
| 6,488,681 B2 * | 12/2002 | Martin et al. | 606/278 |
| 6,565,565 B1 | 5/2003 | Yuan et al. | |
| 6,660,004 B2 * | 12/2003 | Barker et al. | 606/328 |
| 6,869,433 B2 * | 3/2005 | Glascott | 606/308 |
| 6,905,500 B2 * | 6/2005 | Jeon et al. | 606/270 |
| 8,167,916 B2 * | 5/2012 | Saint-Martin | 606/279 |

FOREIGN PATENT DOCUMENTS

| | | |
|---|---|---|
| EP | 0 613 664 A2 | 9/1994 |
| EP | 2276007 A1 | 1/2011 |
| JP | 6-296621 A | 10/1994 |
| JP | 7-59795 | 3/1995 |
| JP | 8-257035 A | 10/1996 |
| JP | 11-318933 A | 11/1999 |
| WO | 96/12976 A1 | 5/1996 |
| WO | 98/27884 A1 | 7/1998 |
| WO | 99/65415 A1 | 12/1999 |
| WO | 01/15612 A1 | 3/2001 |

* cited by examiner

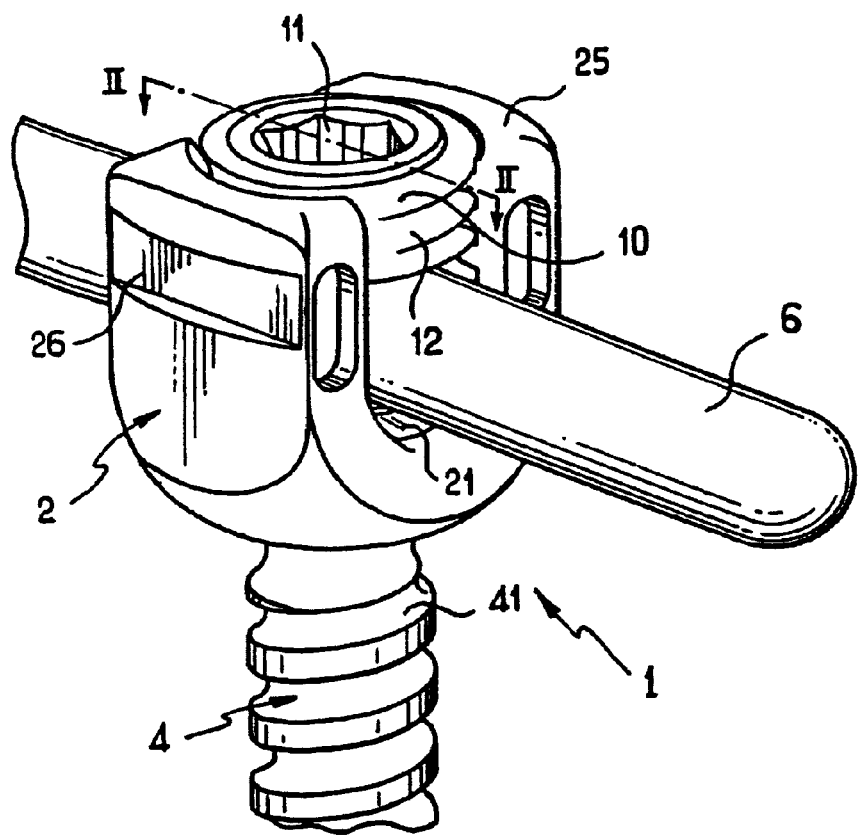
FIG_1
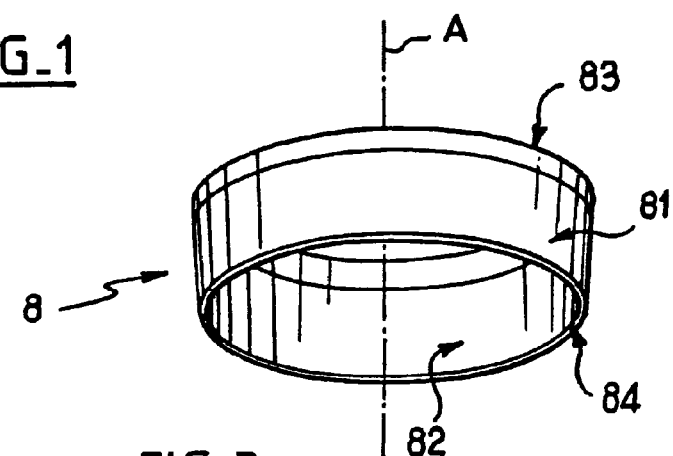
FIG_3

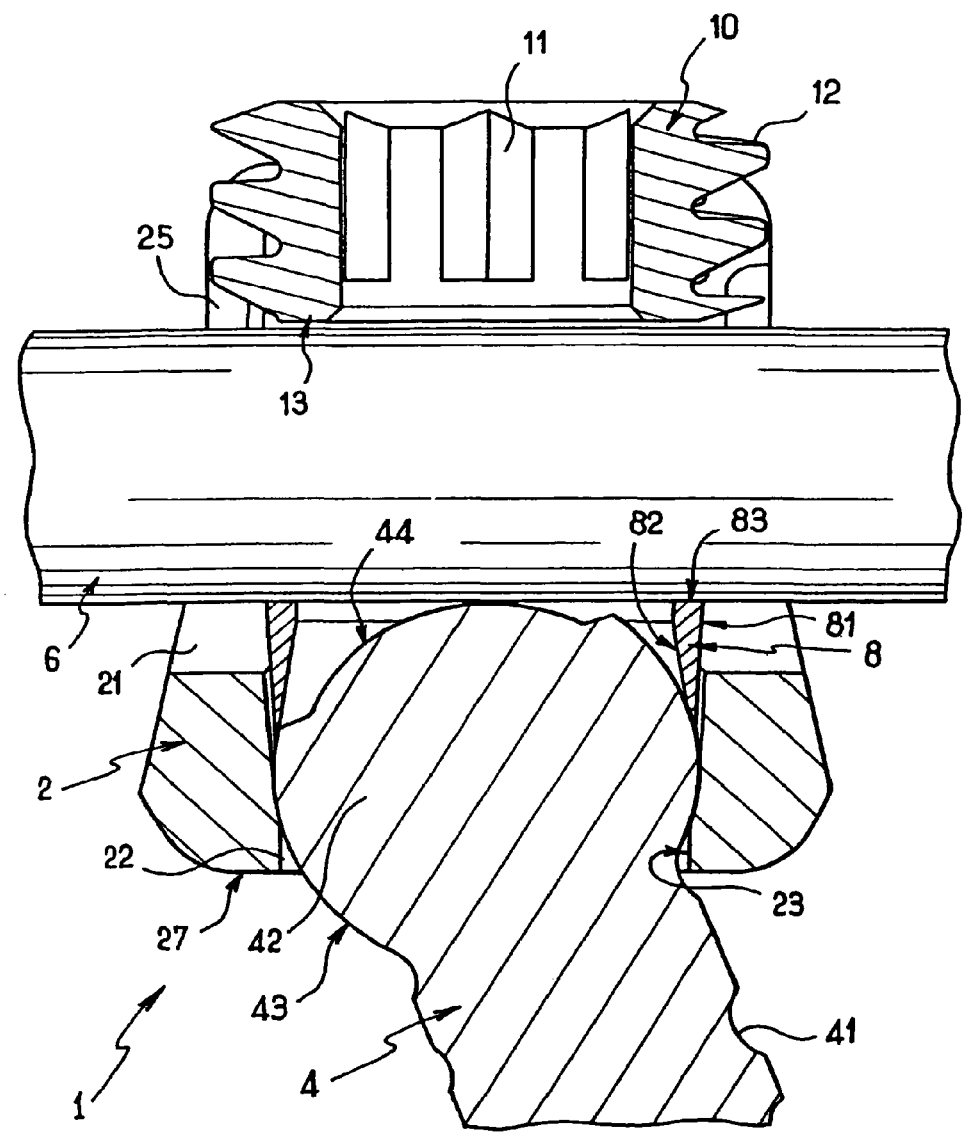
FIG_2

ANCHORING MEMBER WITH SAFETY RING

CROSS REFERENCE TO RELATED APPLICATIONS

The present application is a continuation of application Ser. No. 12/658,838, filed Feb. 16, 2010, which is a continuation of application Ser. No. 10/096,991, filed Mar. 13, 2002, the disclosures of which are incorporated by reference herein.

BACKGROUND OF THE INVENTION

The invention relates to osteosynthesis systems particularly for surgery on the spinal column.

SUMMARY OF THE INVENTION

Document WO 98/12 976 discloses a spinal osteosynthesis system comprising an anchoring member of the polyaxial screw type which is immobilized in position by the link rod bearing against a crown, the rounded lower surface of which bears in a complementary manner on the spherical head of the bone screw lodged in the bottom of a housing made in a connector. Such a system involves a very high bearing force between the rod and the crown in order that the pressure per unit area between the crown and the screw head is high enough to prevent any movement of one with respect to the other, which movement would have the effect of creating instability that is detrimental to the desired osteosynthesis.

SUMMARY OF THE INVENTION

One object of the invention is to provide a position-locking device which is more reliable for the same clamping force.

To do that, an aspect of the invention provides a spinal osteosynthesis assembly comprising a connector, bone anchoring means capable of being received in the connector, a connecting member capable of being received in the connector, and a ring capable of coming into contact with the head, the connecting member being able to come to bear simultaneously against the ring and the head when the ring and the anchoring means are fitted in the connector.

Thus, when locking the osteosynthesis system, the bearing of the connecting member on the ring forces the latter to come to bear against the anchoring means to immobilize the anchoring means in position within the connector, and the simultaneous bearing of the connecting member on the anchoring means enhances the previous immobilization, making it more secure while at the same time maintaining the same clamping force for locking.

Advantageously, the ring has at least one conical face.

Advantageously, the ring has a face able to come into contact with the anchoring means.

Advantageously, the ring has a face able to come into contact with a wall of the connector.

Advantageously, the faces are coaxial.

Advantageously, the ring has a flat upper edge perpendicular to an axis of the ring and able to come into contact with the connecting member.

Advantageously, the ring has a flat lower edge perpendicular to an axis of the ring.

Advantageously, the ring is able to extend between the wall and the anchoring means when the connecting member bears as mentioned.

Advantageously, the ring is deformed when the connecting member bears as mentioned, with reference to the shape that the ring had before fitting.

Advantageously, the ring has a wall thickness which varies according to a height.

Thus, the ring has a cross section in the shape of a wedge which, when the system is locked, simply wedges between the wall of the connector and the anchoring means and this, in a simple way, will further enhance the positional immobilization.

Advantageously, the ring comprises a slot.

Advantageously, the slot is arranged in such a way that the ring forms a non-closed annulus.

Advantageously, the ring comprises a number of slots distributed uniformly about a circumference of the ring.

Advantageously, the anchoring means comprise a head having a roughly spherical face.

Advantageously, the head has a first spherical face and a second spherical face which have the same center and significantly different diameters.

Advantageously, the anchoring means form a polyaxial screw.

Advantageously, the assembly comprises a locking member able to come to bear against the connecting member.

Also provided according to the invention is an osteosynthesis system comprising an assembly exhibiting at least one of the above mentioned features.

BRIEF DESCRIPTION OF THE DRAWINGS

Other features and advantages of the invention will become apparent during the following description of a preferred embodiment. In the appended drawings:

FIG. 1 is a perspective view of the preferred embodiment of the invention;

FIG. 2 is a view: in section on II-II of the embodiment of FIG. 1;

FIG. 3 is a perspective view of the ring of the preferred embodiment;

DETAILED DESCRIPTION

Figure 4:
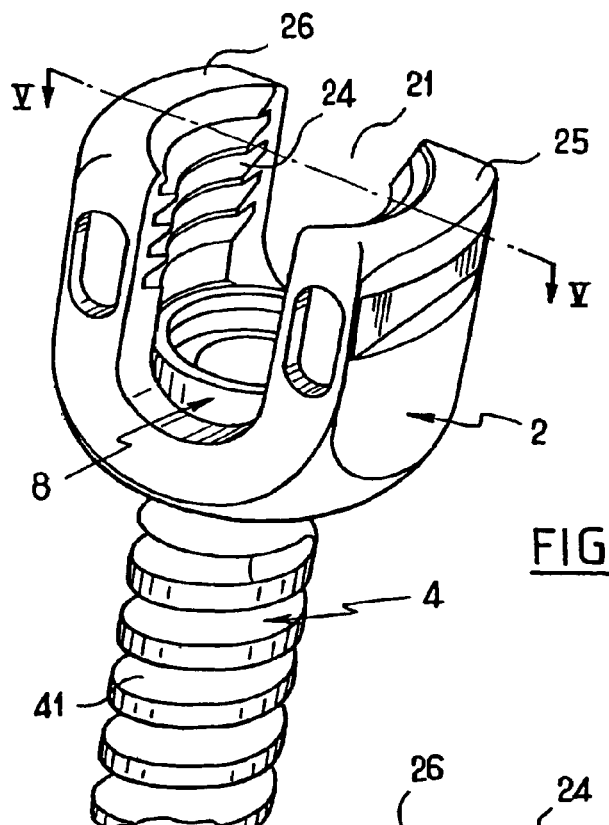
FIG. 4 is a perspective view of the embodiment of FIG. 1 prior to the fitting of the connecting member.

A preferred embodiment will be described with reference to the various FIGS. 1 to 5. The assembly for osteosynthesis of the spinal column 1 here comprises a connector 2, a connecting member 6 and anchoring means 4. Here, the connecting member 6 is an osteosynthesis rod and the anchoring means 4 are formed by a pedicle screw. The assembly 1 also comprises a ring 8 and a locking member 10 capable of locking the assembly 1 in position.

The connector 2 comprises a U-shaped opening 21 forming the upper part of the connector 2. This U-shaped opening 21 is delimited by two branches 25 and 26 which extend roughly parallel with respect to each other. The internal faces of the branches 25 and 26 which extend facing each other comprise a screw thread 24. Furthermore, the connector 2 in its lower part comprises an internal housing 22 having a wall 23. The upper part of the internal housing 22 opens into the bottom of the U-shaped opening 21 and the lower part of the internal housing 22 opens onto a lower face 27 of the connector 2. On the same side as the lower face 27, the wall 23 has a conical section designed so that the opening at the lower face 27 is smaller than the opening at the bottom of the U-shaped opening 21.

The locking member 10 comprises operating means 11 which here are in the form of a through-orifice 11 with a hexagonal socket. This hexagonal socket is designed to accommodate a hexagonal bit fitted to a screwdriver for operating it. Furthermore, the locking member 10 comprises, on its external side wall, a screw thread 12 that complements the screw thread 24 of the connector 2 between the branches 25 and 26 of which it is able to be received.

The anchoring means 4 are here in the form of a pedicle screw comprising an anchoring part 41 exhibiting a bone thread, surmounted by a head 42 which here is roughly spherical. The head 42 has a first spherical surface 43 and, forming the top, a second spherical surface 44, the diameter of which is smaller than the diameter of the spherical surface 43 but has the same center thereas.

Similar osteosynthesis systems can be found in document EP-0 613 664.

The ring 8 is of annular shape and has a first face 82 delimiting the internal wall of the ring, a second face 81 delimiting the external wall of the ring and upper 83 and lower 84 edges perpendicular to the geometric axis of revolution A of the ring 8. The faces 81 and 82 are coaxial and preferably of conical shape. Their respective generators are not mutually parallel. Thus, the faces are arranged one with respect to the other in such a way that the thickness of the ring 2 at the upper edge 83 is greater than the thickness of the ring 8 at the lower edge 84. The cross section of the ring thus has a wedge shape, giving the ring 8 a tapered shape. However, one of the generators of the faces 81 and 82 may be roughly parallel to the axis of revolution A.

Figure 5:
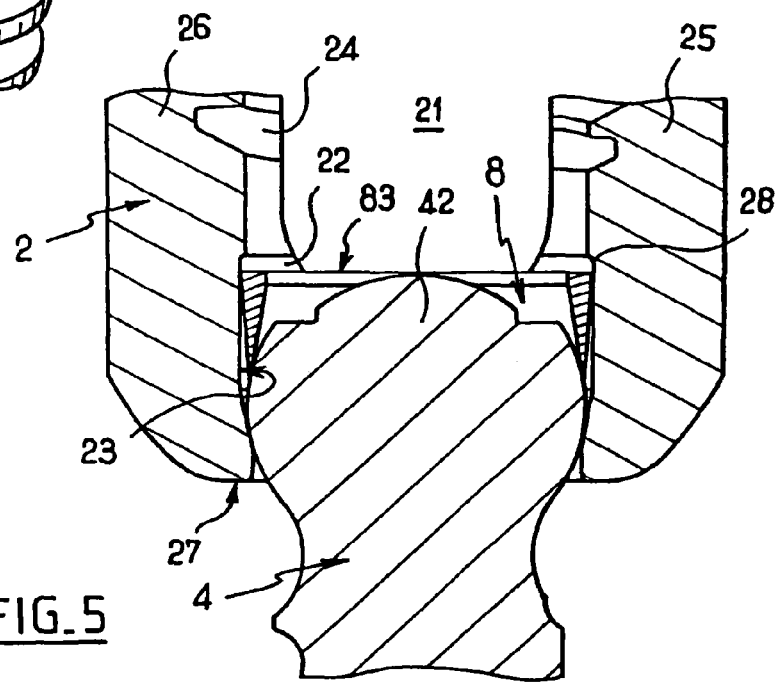
FIG. 5 is a view in section on V-V of the embodiment of FIG. 4.

Prior to use by a surgeon, the connector 2, the anchoring means 4 and the ring 8 are fitted together. More particularly, the head 42 of the anchoring means is inserted into the internal housing 22 of the connector 2. The ring 8 is then itself inserted into the internal housing 22 of the connector 2. Thus, the head 42 of the anchoring means 4 finds itself held captive in the internal housing 22 against exiting upward by the presence, inside the internal housing 22, of the ring 8, which is itself held captive, as will be seen later on. The head 42 is retained against exiting downward by the presence of the conical section of the wall 23 of the internal housing 22, which has an opening at the lower face 27 of the connector 2, the dimensions of which are smaller than the diameter of the surface 43 of the head 42. In addition, the ring 8 is held captive by retaining means 28 present within the internal housing 22. Here, the retaining means 28 stem from the difference in size between the internal housing 22 and the U-shaped opening 21, this difference forming a rim against which the upper edge 83 of the ring 8 abuts from below. This assembly is illustrated in FIGS. 4 and 5.

In use during a surgical operation, the surgeon fits an assembly as described above into the pedicle. He then fits the connecting member 6, inserting it into the U-shaped opening 21 of the connector 2. He then fits the locking member 10 between the branches 25 and 26, engaging the screw thread 12 of the locking member 10 with the complementary screw thread 24 of the connector 2. Using the hexagonal socket 11, he drives the locking member 10 so that the underside 13 of the locking member 10 comes into contact with the connecting member 6.

By continuing to screw the locking member 10 between the branches 25 and 26, the surgeon will exert a force via the locking member 10 on the connecting member 6, and this will push the connecting member 6 until the latter comes to bear against the upper edge 83 of the ring 8.

As locking continues, the ring 8 then slips along the wall 23 of the internal housing 22 until the face 82 of the ring 8 comes into contact with the surface 43 of the head 42 of the anchoring means 4. The surface 43 is itself in contact with the conical section of the wall 23 of the internal housing 22 of the connector 2. The system therefore finds itself in a situation as illustrated in FIG. 2.

During final locking, which will allow the assembly to be immobilized in position, the clamping force imparted by the surgeon via the locking member 10 will allow the ring 8 to be made to slide on the head 42. For that, the face 82 will slide on the surface 43, forcing the ring 8 to open up by deformation until the face 81 of the ring 8 comes into contact over all or part of its surface with the wall 23 of the internal housing 22 of the connector 2. At that moment, the connecting member 6 comes to bear at a point on the spherical surface 44. Thus, the head 42 is immobilized in position, on the one hand, by the ring 8 and, on the other hand, by the connecting member 6 directly. There is thus what is known as three-point contact, two of the points being diametrically opposed points of contact of the edge 83 of the ring 8 with the connecting member 6 and one additional point where the connecting member 6 contacts the surface 44 of the head 42 of the anchoring means 4.

Of course, numerous modifications could be made to the invention without departing from its scope.

Figure 6:
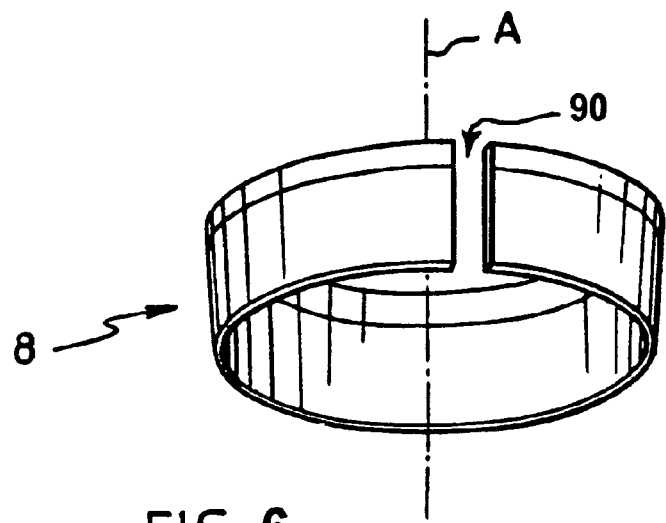
FIG. 6 is a perspectives view of an embodiment of the ring as a non-closed annulus.

For example, referring to FIG. 6, the ring 8 could have at least one slot 90. This slot could be arranged in such a way that the ring forms a non-closed annulus.

Figure 7:
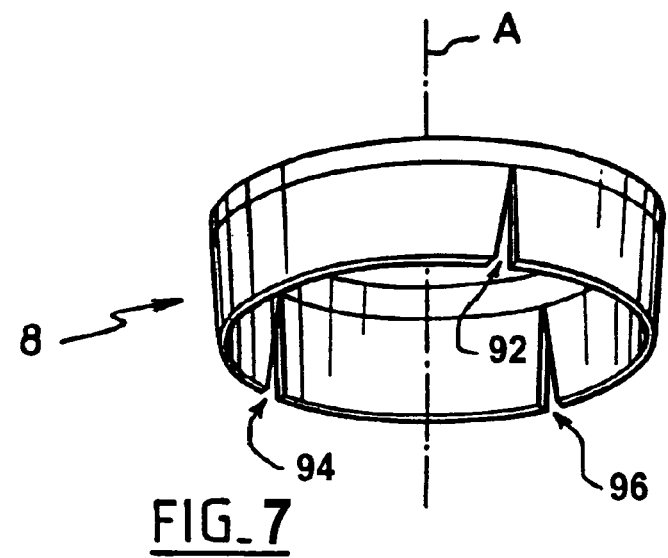
FIG. 7 is a perspective view of an embodiment of the ring with circumferential slots.

Alternately, referring to FIG. 7, the tapered shape due to the wedge shape of the cross section of the ring, instead of being continuous over its entire circumference, could consist of a number of sectors separated by slots 92, 94 and 96 to form an "umbrella" structure.

These various modifications allow easier deformation of the ring 8. This has the effect of making the ring 8 easier to introduce into the internal housing 22 of the connector 2, on the one hand, and, on the other hand, of making the final locking during use in a surgical operation easier.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method for osteosynthesis of a spinal column using an assembly including a bone anchor, a connector, a ring and a connecting member, the method comprising:
   inserting an anchoring part of the bone anchor into bone, the bone anchor including the anchoring part and a head, the head positioned to be in contact with the connector and ring;
   inserting the connecting member into the connector; and
   applying a force to the connecting member such that the connecting member applies the force against the ring and the bone anchor, wherein the head of the bone anchor contacts the connector, ring and connecting member during the application of the force.

2. The method of claim 1, wherein the step of applying the force to the connecting member comprises fitting a locking member into the connector such that the locking member applies the force against the connecting member, ring and bone anchor.

3. The method of claim 2, wherein the connector further comprises a screw thread and the locking member further comprises a screw thread complimentary to the screw thread of the connector wherein threading the locking member into the connector applies the force.

4. The method of claim 1, wherein the ring deforms when the connecting member applies the force against the ring and the bone anchor.

5. The method of claim 4, wherein the ring comprises at least one slot distributed about a circumference of the ring.

6. The method of claim 4, wherein at least a portion of the ring is forced at least partially between the bone anchor and the connector.

7. The method of claim 6, wherein the ring has at least one conical face in cross-section and the head of the bone anchor includes a spherical surface such that the application of the force positions the conical face of the ring to be in contact with the spherical surface of the head of the bone anchor.

8. The method of claim 1 wherein the application of the force immobilizes the head of the bone anchor in a three-point contact.

9. The method of claim 8, wherein the three-point contact comprises the contact of the connecting member and the head of the bone anchor and the contact at two diametrically opposed points of contact on an upper edge of the ring with the connecting member.

10. The method of claim 1, wherein the head of the bone anchor has a polyaxial range of motion and the connecting member is positioned in the connector such that it applies the force against the ring and bone anchor throughout the polyaxial range of motion of the bone anchor.

11. A method for osteosynthesis of a spinal column using an assembly comprising a bone anchor, a ring, a connecting member, and a connector, the method comprising:
    positioning an anchoring part of the bone anchor in bone, the bone anchor including the anchoring part and a head, the head positioned to be in contact with the connector and ring;
    assembling the connecting member in the connector such that the bone anchor, ring and connecting member are arranged to be tightened against each other in the connector; and
    tightening the assembly by applying a force on the connecting member such that the connecting member contacts the ring and the head of the bone anchor.

12. The method of claim 11, wherein the head of the anchoring member, after the tightening step, contacts each of the connector, ring and connecting member.

13. The method of claim 11, wherein the application of force to the connecting member comprises fitting a locking member into the connector such that the locking member applies the force against the connecting member, ring and bone anchor.

14. The method of claim 13, wherein the connector further comprises a screw thread and the locking member further comprises a screw thread complimentary to the screw thread of the connector wherein threading the locking member into the connector applies the force.

15. The method of claim 11, wherein the ring deforms when the connecting member applies the force against the ring and the bone anchor.

16. The method of claim 15, wherein the ring comprises at least one slot distributed about a circumference of the ring.

17. The method of claim 15, wherein at least a portion of the ring being forced at least partially between the bone anchor and the connector.

18. The method of claim 17, wherein the ring has at least one conical face in cross-section and the head of the bone anchor includes a spherical surface such that the application of the force positions the conical face of the ring to be in contact with the spherical surface of the head of the bone anchor.

19. The method of claim 11 wherein the application of the force immobilizes the head of the bone anchor in a three-point contact, the three-point contact comprising the contact of the connecting member and the head of the bone anchor and the contact at two diametrically opposed points of contact on an upper edge of the ring with the connecting member.

20. The method of claim 11, wherein the head of the bone anchor has a polyaxial range of motion and the connecting member is positioned in the connector such that it applies the force against the ring and bone anchor throughout the polyaxial range of motion of the bone anchor.

* * * * *